United States Patent
Fojtik et al.

(10) Patent No.: US 10,653,553 B2
(45) Date of Patent: May 19, 2020

(54) THERMAL CONTROL SYSTEM WITH FLUID CARTRIDGES

(71) Applicant: Stryker Corporation, Kalamazoo, MI (US)

(72) Inventors: Erika Grace Fojtik, Kalamazoo, MI (US); Martin W. Stryker, Kalamazoo, MI (US); Gregory S. Taylor, Kalamazoo, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 143 days.

(21) Appl. No.: 15/880,721

(22) Filed: Jan. 26, 2018

(65) Prior Publication Data

US 2018/0214301 A1    Aug. 2, 2018

Related U.S. Application Data

(60) Provisional application No. 62/451,121, filed on Jan. 27, 2017.

(51) Int. Cl.
*A61F 7/00*    (2006.01)
*A61F 7/02*    (2006.01)

(52) U.S. Cl.
CPC .............. *A61F 7/0085* (2013.01); *A61F 7/02* (2013.01); *A61F 2007/0054* (2013.01)

(58) Field of Classification Search
CPC ...... A61F 2007/0054; A61F 2007/0056; A61F 7/0085; A61F 7/02
See application file for complete search history.

(56) References Cited

U.S. PATENT DOCUMENTS

| | | |
|---|---|---|
| 6,261,261 B1 | 7/2001 | Gordon |
| 6,620,189 B1 | 9/2003 | Machold et al. |
| 6,673,098 B1 | 1/2004 | Machold et al. |
| 6,830,581 B2 | 12/2004 | Magers |
| 6,878,156 B1 | 4/2005 | Noda |
| 7,258,662 B2 | 8/2007 | Machold et al. |
| 7,666,215 B2 | 2/2010 | Callister et al. |

(Continued)

OTHER PUBLICATIONS

Stryker, Altrix Precision Temperature Management System, Operations Manual, Dec. 2016.

(Continued)

*Primary Examiner* — Kaitlyn E Smith
*Assistant Examiner* — Bradford C. Blaise
(74) *Attorney, Agent, or Firm* — Warner Norcross + Judd LLP (57) ABSTRACT

A thermal control system for controlling a temperature of a fluid delivered to a patient is provided. The thermal control system includes a cavity that removably receives a cartridge housing the fluid. The thermal control system includes a heat exchanger in thermal contact with at least one of the opposing walls of the cavity. The cartridge includes opposing surfaces defining a chamber therebetween for housing the fluid, the cartridge adapted to be removably received within the cavity. A biasing element is incorporated into the cartridge and adapted to bias the opposing cartridge surfaces away from one another and into contact with the opposing cavity walls. Contact between the cartridge surfaces and the cavity walls facilitates the transfer of thermal energy between the heat exchanger and the fluid housed within the cartridge.

21 Claims, 7 Drawing Sheets

(56) References Cited

U.S. PATENT DOCUMENTS

| | | |
|---|---|---|
| 8,100,957 B2 | 1/2012 | Callister et al. |
| 8,128,595 B2 | 3/2012 | Walker et al. |
| 8,313,461 B2 | 11/2012 | Walker et al. |
| 8,870,819 B2 | 10/2014 | Walker et al. |
| 8,968,378 B2 | 3/2015 | Ginsburg et al. |
| 9,259,349 B2 | 2/2016 | Walker et al. |
| 9,278,024 B2 | 3/2016 | Scott et al. |
| 9,314,367 B2 | 4/2016 | Callister et al. |

OTHER PUBLICATIONS

Medivance, Arctic Sun 5000, Service Manual, 2010-2011.
Gaymar, Medi-Therm III Hyper/Hypothermia Machine REF MTA7912, Service Manual, 2009.
Sorin Group, Heater-Cooling System 3T, Operating Instructions, Feb. 2015.

THERMAL CONTROL SYSTEM WITH FLUID CARTRIDGES

CROSS-REFERENCE TO RELATED APPLICATIONS

This application claims priority to U.S. provisional patent application Ser. No. 62/451,121 filed Jan. 27, 2017, by inventors Martin Stryker et al. and entitled THERMAL CONTROL SYSTEM WITH FLUID CARTRIDGES, the complete disclosure of which is incorporated herein by reference.

BACKGROUND

The present disclosure relates to a thermal control system for controlling the temperature of circulating fluid which is delivered to one or more thermal pads positioned in contact with a patient.

Thermal control systems are known in the art for controlling the temperature of a patient by supplying temperature-controlled fluid to one or more pads, blankets, or similar structures, that are positioned in contact with, or adjacent to, a patient. The temperature of the fluid is controlled by a thermal unit that provides fluid to the pads or blankets. After passing through the pads or blankets, the fluid is returned to the control unit where any necessary adjustments to the returning fluid temperature are made before being pumped back to the pad or blanket. In some instances, the temperature of the fluid is controlled to a target fluid temperature, while in other instances the temperature of the fluid is controlled in order to effectuate a target patient temperature. When controlling a patient's temperature, a patient temperature probe may be attached to the control unit in order to provide patient temperature readings as feedback to the control unit so that it can make the necessary temperature adjustments to the circulating fluid.

In some instances, the thermal control system includes a thermal control unit, a cartridge insertable into the thermal control unit, and one or more pads or blankets that are fluidly coupled to the cartridge. The use of a cartridge inside the thermal control unit ensures physical isolation between the thermal control unit and the circulating fluid. After use, the thermal cartridge is removed from the thermal control unit and a fresh thermal cartridge is inserted for the subsequent use. By maintaining the physical separation between the circulating fluid and the thermal control unit, any bacteria or other undesirable substances within the fluid does not remain in the thermal control unit after use.

SUMMARY

The present disclosure provides various improved aspects to a thermal control system. In one embodiment, the present disclosure includes a thermal control unit and a fluid cartridge that is configured to be secured within a cavity of the thermal control unit in a single motion, without any additional movement or steps required of the user to secure the fluid cartridge in place. The thermal control unit cavity includes angled walls and the fluid cartridge includes angled surfaces that are adapted to match the angled cavity walls when the fluid cartridge is inserted into the cavity to promote contact between the cavity walls and the cartridge surfaces to facilitate the transfer of thermal energy therebetween. The fluid cartridge includes a hinge that allows the cartridge surfaces to be pressed together to provide clearance to insert the fluid cartridge into the cavity.

In some embodiments, the cartridge surfaces are biased into contact with the cavity walls to promote contact between the cartridge surfaces and the cavity walls. In other embodiments, the cartridge surfaces are biased such that releasing the cartridge surfaces after insertion into the cavity retains the fluid cartridge within the cavity in a single step, without any additional user-movement or steps required to secure the fluid cartridge in place. In still other embodiments, a biasing element is incorporated into the cavity or the cartridge that exerts a first force in a first direction. The first force is redirected at least partially into a second direction that urges the cartridge surfaces into contact with the cavity walls.

According to one embodiment, a thermal control system for controlling a temperature of a fluid delivered to a patient is provided. The thermal control system includes a housing having a cavity with opposing walls. A heat exchanger is positioned within the housing and in thermal contact with at least one of the opposing walls of the cavity. The thermal control system also includes a cartridge having opposing surfaces that define a chamber therebetween for housing the fluid. The cartridge is adapted to be removably received within the cavity. A biasing element is incorporated into the cartridge and adapted to bias the opposing surfaces away from one another and into contact with the opposing walls of the cavity. When the cartridge is received within the cavity, thermal energy can be transferred between the heat exchanger and the fluid housed within the cartridge.

In other aspects, the biasing element includes a spring or a living hinge.

In some embodiments, the thermal control system includes a tab incorporated into one of the cavity or the cartridge. The other of the cavity or the cartridge includes a mating slot. When the cartridge is inserted into the cavity, the tab engages the slot and retains the cartridge within the cavity. In some aspects, the tab is biased toward the slot. In still other aspects, the cartridge includes a pair of projections that extend beyond an opening to the cavity when the cartridge is received within the cavity. The projections are adapted to be grasped to press the cartridge surfaces toward one another, against the bias, to disengage the tab from the slot.

In other aspects, the thermal control system includes cartridge surfaces having a flexible portion adapted to expand outward under pressure.

According to another embodiment, a thermal control system is provided that includes a housing having a cavity with opposing walls and an opening therebetween. The opposing walls are oriented at a first angle relative to one another such that a distance between the opposing walls decreases with increasing depth in the cavity. A heat exchanger is positioned within the housing and in thermal contact with at least one of the opposing walls of the cavity. The thermal control system includes a cartridge having a pair of opposing surfaces defining a chamber therebetween for housing the fluid. The cartridge is adapted to be removably received within the cavity through the opening. The opposing cartridge surfaces are oriented at a second angle relative to one another, and the second angle is greater than the first angle. When the cartridge is received within the cavity, one or both of the first and second angles change to match the other. Further, when the cartridge is received within the cavity, thermal energy is transferred between the heat exchanger and the fluid housed within the cartridge.

In other aspects, the cartridge surfaces are adapted to deflect as the cartridge is inserted into the cavity through the opening. In still other aspects, the cartridge includes a biasing element that biases the cartridge surfaces toward the second angle. The cartridge surfaces are moveable toward one another, against the bias, to a third angle at least as small as the first angle. The biasing element can include a spring or a living hinge formed in the cartridge.

According to another embodiment, a thermal control system is provided that includes a housing having a cavity with opposing walls and an opening therebetween. A heat exchanger is positioned within the housing and in thermal contact with at least one of the opposing walls of the cavity. A cartridge includes opposing surfaces defining a chamber therebetween for housing the fluid. The cartridge is adapted to be removably received within the cavity through the opening. A biasing element is incorporated into one of the housing or the cartridge and adapted to exert a first force in a first direction toward the opening. The cartridge is adapted to respond to the first force by redirecting a component of the first force in a second direction different from the first direction. The second force urges the cartridge surfaces into contact with the opposing walls such that when the cartridge is received within the cavity, thermal energy is transferred between the heat exchanger and the fluid housed within the cartridge.

In other aspects, the cavity walls are oriented at a first angle relative to one another. The cartridge surfaces are oriented at a second angle relative to one another, the second angle greater than the first angle. When the cartridge is received within the cavity, one or both of the first and second angles change to match a common angle.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
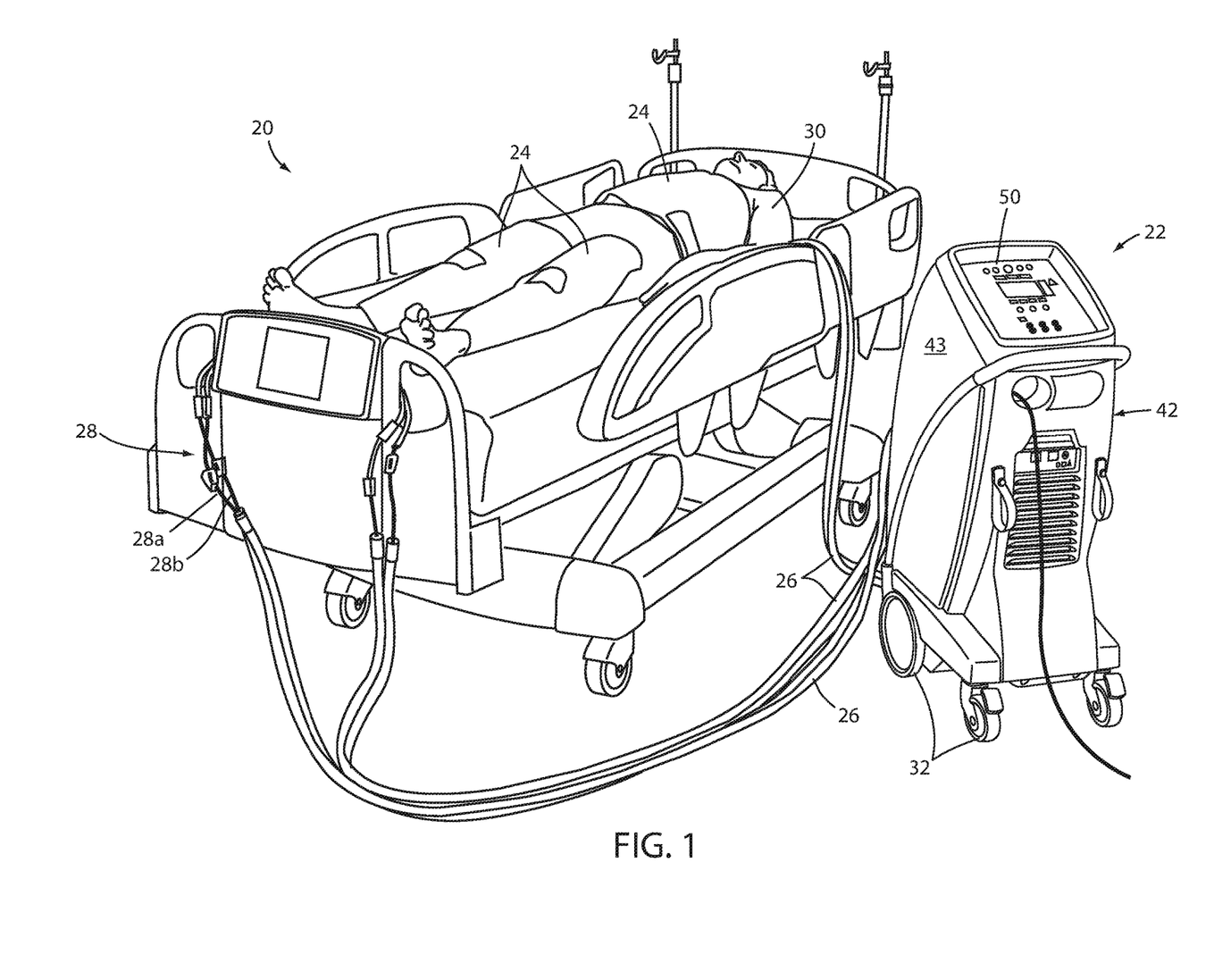
FIG. 1 is a perspective view of a thermal control system according to the present disclosure that may be used to provide thermal treatment to a patient.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each hose includes one or more fluid lines 28. In the embodiment shown in FIG. 1, each hose 26 includes a fluid supply line 28a and a fluid return line 28b. Thermal control unit 22 delivers temperature controlled fluid (such as, but not limited to, water) to thermal pads 24 via supply lines 28a. After the temperature controlled fluid has passed through thermal pads 24, thermal control unit 22 receives the temperature controlled fluid back from thermal pads 24 via return lines 28b.

In some embodiments, thermal control system 20 includes a plurality of auxiliary lines adapted to couple to thermal control unit 22. Such auxiliary lines may be used in different manners, depending upon the capabilities of thermal control unit 22, the construction of one or more of the thermal pads 24, and/or the desired treatment to be applied to the patient 30. Such auxiliary lines may be used to deliver a pressurized gas (such as, but not limited to, air) to thermal pads 24, to generate negative gauge pressure at the thermal pad 24 (either inside one or more chambers of the thermal pads 24 or in the ambient surroundings of the thermal pads 24), or for other purposes. The use of such auxiliary lines is described in greater detail in commonly assigned U.S. patent application Ser. No. 62/373,658 filed Aug. 11, 2016, by inventors James Galer et al. and entitled THERMAL THERAPY DEVICES, the complete disclosure of which is incorporated herein by reference.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply lines 28a, the temperature of the patient 30 can be controlled via the close contact of the pads 24 with the patient 30 and the resultant heat transfer therebetween. In some embodiments, thermal pads 24 are constructed in accordance with any of the constructions disclosed in either of the following commonly assigned U.S. patent applications: Ser. No. 62/373,564 filed Aug. 11, 2016, by inventors James Galer and entitled THERMAL SYSTEM; and Ser. No. 62/373,658 filed Aug. 11, 2016, by inventors James Galer et al. and entitled THERMAL THERAPY DEVICES, the complete disclosures of both of which are incorporated herein by reference.

Although thermal control unit 22 has been shown and described herein as having wheels 32 for pushing thermal control unit 22 to different locations, it will be understood that the cartridges disclosed herein are able to be used in more mobile thermal control units that are adapted to be carried from location to location. One such portable thermal control unit is disclosed in commonly assigned U.S. patent application Ser. No. 62/311,054 filed Mar. 21, 2016, by inventor Gregory Taylor and entitled MOBILE THERMAL SYSTEM, the complete disclosure of which is incorporated herein by reference.

Thermal control unit 22 is adapted, in the illustrated embodiment, to operate in a plurality of different modes that are selectable by a user. In a first mode, known as a manual mode, thermal control unit 22 controls the temperature of the liquid circulating through control unit 22—and thereby the temperature of the fluid delivered to thermal pads 24—so that it matches a target temperature chosen by the user. In this mode, the control unit 22 maintains the liquid at the chosen target temperature regardless of the patient's temperature. Indeed, in the manual mode, control unit 22 may be used without any patient temperature probes. In a second mode, known as an automatic mode, thermal control unit 22 controls the temperature of the liquid circulating through control unit 22 in such a manner that a target patient temperature is achieved and/or maintained. In this automatic mode, at least one patient temperature probe must be coupled to control unit 22 so that control unit 22 knows the patient's current temperature. In the automatic mode, control unit 22 does not necessarily adjust the temperature of the circulating fluid to maintain a constant temperature, but instead makes the necessary temperature adjustments to the fluid in order to effectuate the desired patient temperature.

When thermal control system 20 is adapted to operate in the automatic mode, it includes one or more patient temperature probes that are attached to locations of thermal interest on a patient. Such patient temperature probes may be any suitable patient temperature probe that is able to sense the temperature of the patient at the location of the probe. In one embodiment, the patient temperature probes are conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in system 20, each temperature probe is connected to a patient temperature probe port (not shown) positioned on control unit 22. Patient temperature probe ports are in electrical communication with a controller 40 (FIG. 2) that is adapted, in at least some situations, to use the temperature sensed by at least one of the probes in controlling the temperature of the fluid circulated through control unit 22 and pads 24.

Figure 2:
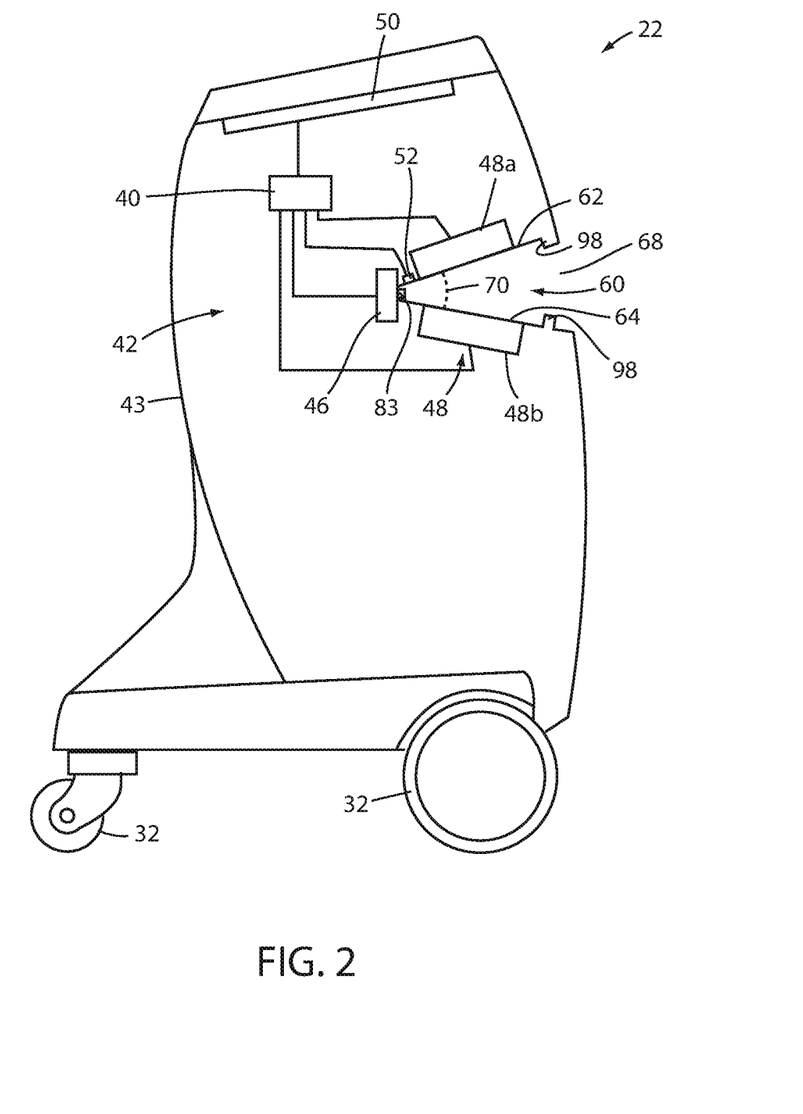
FIG. 2 is a side view schematic of the thermal control unit of the thermal control system of FIG. 1.

Referring now to FIG. 2, thermal control unit 22 includes a main body 42 having an external housing 43. Positioned within external housing 43 is a controller 40 in electrical communication with a variety of different sensors and/or actuators. More specifically, controller 40 is in electrical communication with a motor 46, a heat exchanger 48, a control panel 50 (FIG. 1), and one or more temperature sensors 52 that measure the temperature of the circulating fluid. Control panel 50 allows a user to operate thermal control unit 22, including setting a desired fluid target temperature and/or a desired patient target temperature, and/or to control other aspects of thermal control unit 22. The temperature sensors 52 provide feedback to controller 40 that enables controller 40 to adjust heat exchanger 48, as appropriate, in order to effectuate closed-loop control of the temperature of the circulating fluid. Temperature sensors 52 can be any suitable contact or non-contact temperature sensor, non-limiting examples of which include negative temperature coefficient (NTC) thermistors, resistance temperature detectors (RTD), thermocouples, semiconductor-based sensors, and infrared sensors.

Controller 40 includes any and all electrical circuitry and components necessary to carry out the functions and algorithms described herein, as would be known to one of ordinary skill in the art. Generally speaking, controller 40 may include one or more microcontrollers, microprocessors, and/or other programmable electronics that are programmed to carry out the functions described herein. It will be understood that controller 40 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

Controller 40 uses the outputs of the one or more temperature sensors 52 to control the temperature of the circulating fluid such that the circulating fluid has its temperature adjusted (or maintained) in accordance with the operating mode (manual or automatic) selected by the user of thermal control unit 22. Controller 40 may control the temperature of the fluid using a closed loop proportional-integral (PI) controller, a closed-loop proportional-integral-derivative (PID) controller, or some other type of closed-loop controller. In some embodiments, the thermal control unit 22 includes additional sensors, non-limiting examples of which include pressure sensors for determining a pressure of the circulating fluid and a flow rate sensor for determining a rate of flow of the circulating fluid.

Thermal control unit 22 is adapted to raise or lower the temperature of the fluid supplied to thermal pads 24 via supply lines 28a. Thermal control unit 22 includes a cavity 60 having a first cavity wall 62 and an opposing second cavity wall 64. First and second cavity walls 62 and 64 are configured to receive a fluid cartridge 66 (FIG. 2) through which fluid is circulated. Cavity 60 includes an opening 68 between first and second cavity walls 62, 64 through which fluid cartridge 66 can be inserted. First and second cavity walls 62, 64 extend inwardly into thermal control unit 22 from opening 68 toward one another at an angle 70 such that a distance between opposing cavity walls 62, 64 decreases with increasing depth into cavity 60.

Fluid is circulated through fluid cartridge 66 via supply lines 28*a* to thermal pads 24. After the fluid has passed through thermal pads 24, the fluid returns to the fluid cartridge 66 via return lines 28*b*. Cavity 60 and fluid cartridge 66 are configured such that when fluid cartridge 66 is received within cavity 60, the fluid within the fluid cartridge 66 can be heated or cooled by its close contact with heat exchanger 48. Heat exchanger 48 includes a first portion 48*a* in thermal contact with first cavity wall 62 and a second portion 48*b* in thermal contact with second cavity wall 64. The number, shape, and size of heat exchanger 48 can vary as needed. In some embodiments, heat exchanger 48 may include only a single portion in contact with only one wall of cavity 60.

Figure 3:
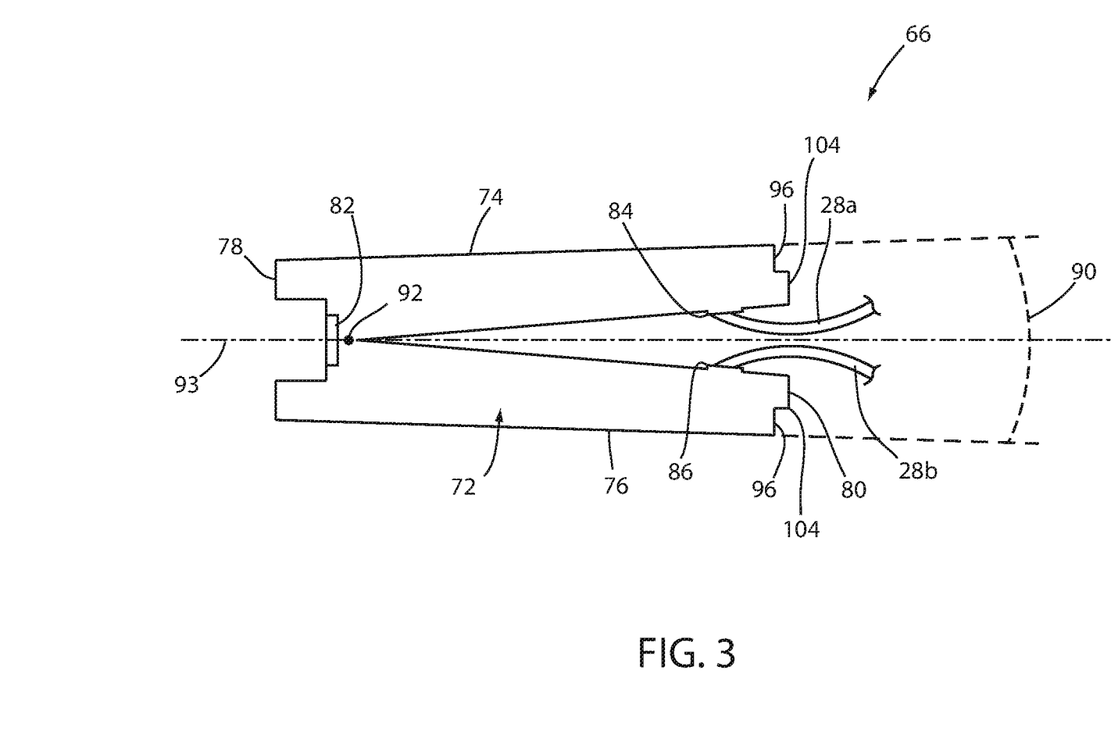
FIG. 3 is a cross-sectional schematic view of a fluid cartridge insertable into the thermal control unit of FIG. 2.

It will be understood that in order to better transfer thermal energy between heat exchanger 48 and the fluid contained with cartridge 66, the bottom of heat exchanger portion 48*a* may partially or wholly define cavity wall 62 and the top of heat exchanger portion 48*b* may partially or wholly define cavity wall 64. Further, although FIG. 3 illustrates cavity walls 62 and 64 as being generally flat, this need not be the case. In some embodiments, cavity walls 62 and 64 may be curved, undulating, discontinuous, and/or otherwise changed from the generally flat and continuous structures illustrated in FIG. 3.

When heat exchanger portions 48*a* and 48*b* partially or wholly define cavity walls 62 and/or 64, and if heat exchanger portion 48*a* or 48*b* are adapted to use a refrigerant to remove heat, the refrigerant of the heat exchanger portion is separated from cartridge surface 74 or 76 only by an adjacent portion of the cavity wall 62 or 64 (which forms the heat exchanger boundary). When heat exchanger portions 48*a* and 48*b* partially or wholly define cavity walls 62 and/or 64, and if the heat exchanger portion is adapted to provide heat, the heating element may be positioned directly in contact with cavity wall 62 or 64 (or in some cases, may be integrated into, or the same as, cavity wall 62 or 64). Thus, for example, if the heat exchanger is implemented as one or more thermoelectric plates, one or more of the plates may define all or a portion of cavity walls 62 and 64.

By having heat exchanger portions 48*a* and/or 48*b* define all or a portion of cavity walls 62 and/or 64, the amount of material and/or layers of material between the heat source or heat sink (contained in the heat exchanger portions 48*a* and/or 48*b*) and the adjacent cartridge surfaces 74 and 76 can be reduced. That is, there is no need to include both an exterior heat exchanger wall and a cavity wall (62 or 64) between cartridges surfaces 74 and 76 and the heat sink and/or heat source of the heat exchanger portions. This construction reduces the amount of physical material that must be traversed by the heat flowing between heat exchanger portions 48*a* and 48*b* and cartridge 66. Consequently, it will be understood that the term "cavity wall" used herein may refer to both a structure separate from a heat exchanger as well as a structure that is wholly or partially defined by one or more heat exchangers.

In some alternative embodiments, however, it will be understood that heat exchanger portions 48*a* and/or 48*b* include external walls that are separate from and additional to cavity walls 62 and 64. In these alternative embodiments, heat passing between cartridge 66 and the heat exchanger portions must traverse two walls: a heat exchanger wall and a cavity wall. Regardless of the number walls used in any of the embodiments, the walls are generally thin and made of materials with good heat conductivity properties, such as, but not limited to, metal and/or metal foil.

As noted above, in some embodiments, one or both of heat exchanger portions 48*a* and 48*b* include a thermoelectric plate adapted to heat and/or cool the fluid within cartridge 66. One or more other types of heaters may be additionally or alternatively used, such as, but not limited to, a resistive heater, a radiant heater, an induction-based heater, a microwave heater, and a thermoelectric heat pump. Heat exchanger portions 48*a* and/or b may also include a cooling device, such as a thermoelectric or Peltier cooler, a vapor-compression refrigeration device, or other device that is configured to cool the fluid within cartridge 66. In some embodiments, first portion 48*a* and second portion 48*b* are separately controllable by controller 40 such that one portion is configured to heat the fluid within cartridge 66 while the other portion is configured to cool the fluid within cartridge 66. In other embodiments, one or both of first portion 48*a* and second portion 48*b* include both a source of heat and a source of cooling.

Referring now to FIG. 3, fluid cartridge 66 includes a fluid chamber 72 defined in part by a pair of opposing cartridge surfaces 74 and 76, a rear end 78, and a front end 80. A pump head 82 is located within chamber 72, adjacent rear end 78, and is configured to pump the fluid through chamber 72. Pump head 82 can include an impeller (not shown) adapted to circulate fluid through chamber 72. Rear end 78 is configured to mate with motor 46 in thermal control unit 22 such that pump head 82 engages a suitable pump driver 83 that is operably engaged with motor 46 to rotate the impeller to circulate the fluid. In alternative embodiment, a peristaltic pump may be included within fluid cartridge 66 and a roller included in the body of thermal control unit 22 that powers the peristaltic pump. Still other types of pumps and pump drivers may be used.

Fluid cartridge 66 further includes a fluid outlet 84 that is adapted to fluidly couple to a supply line 28*a* and a fluid inlet 86 that is adapted to fluidly couple to a return line 28*b*. Fluid is circulated through chamber 72 by pump head 82 and into supply line 28*a* through fluid outlet 84. Fluid travels through supply line 28*a* to thermal pad 24 and returns to chamber 72 via return line 28*b* and fluid inlet 86. In some embodiments, multiple fluid outlets 84 and fluid inlets 86 are provided for fluidly coupling chamber 72 with multiple supply and return lines 28*a*, 28*b*. In other embodiments, a fluid outlet 84 and fluid inlet 86 are coupled to a fluid manifold to which multiple supply and return lines 28*a*, 28*b*, respectively, are connected.

Fluid cartridge 66 is constructed such that the fluid entering and exiting inlet and outlet 86 and 84, respectively, remains physically isolated from thermal control unit 22 at all times. That is, the fluid within cartridge 66 (including chamber 72) never comes in physical contact with any portion of thermal control unit 22. By maintaining this fluid isolation, no fluid is left inside of thermal control unit 22 after cartridge 66 is removed. This helps prevent the growth of any bacteria in thermal control unit 22. Further, to the extent any such growth did occur, the physical isolation of the fluid within cartridge 66 from the interior of thermal control unit 22 prevents such bacteria from entering the fluid and being carried by the fluid to the patient.

Cartridge surfaces 74 and 76 are configured to efficiently transfer thermal energy between heat exchanger 48 and the fluid within chamber 72 when cartridge 66 is received within cavity 60. Cartridge surfaces 74 and 76 are oriented at an angle 90 relative to one another that is greater than angle 70 of cavity walls 62, 64. The body of cartridge 66 is configured such that cartridge surfaces 74 and 76 are pivotable relative to one another about a pivot axis 92 that extends into and out of the plane of FIG. 3. It will be understood that cartridge 66 can be constructed such that pivot axis 92 is positioned in different locations from what is shown in FIG. 3. In some embodiments, pivot axis 92 may be positioned rearwardly of rear end 78 at any location that intersects a midline 93. As a result of this pivoting, angle 90 is able to increase and decrease. When angle 90 decreases, cartridges surfaces 74 and 76 move closer to each other toward a midline 93, and when angle 90 increases, cartridge surfaces 74 and 76 move further away from midline 93. A decrease in angle 90 provides clearance for insertion of fluid cartridge 66 through opening 68. The angle 90 of cartridge 66 shown in FIG. 3 corresponds to a neutral angle of cartridge 66. That is, this is the angle that cartridge 66 attempts to return to if it is flexed to a greater or smaller angular orientation.

Cartridge surfaces 74 and 76 can be hingedly connected to the body of cartridge 66 such that cartridge surfaces 74 and 76 are able to pivot or flex about axis 92. In one embodiment, portions of cartridge 66 are made from a flexible polymeric material including one or more living hinges configured to allow cartridge surfaces 74 and 76 to pivot about axis 92 to change angle 90. In other embodiments, mechanical hinges are used to allow cartridge surfaces 74 and 76 to pivot about axis 92. In still other embodiments, cartridge 66 is made of an inherently flexible material that allows surfaces 74 and 76 to be flexed toward or away from each other sufficiently to allow cartridge 66 to be inserted into cavity 60. Regardless of the specific manner in which the flexibility of cartridge 66 is designed, cartridge 66 is constructed to resist the pivoting of surfaces 74 and 76 about axis 92 to angles other than the neutral value of angle 90 shown in FIG. 3. That is, cartridge 66 is configured to return to the unflexed or neutral state of FIG. 3. Movement out of this neutral state is resisted by the internal construction of cartridge 66 and creates an internal biasing force that urges surfaces 74 and 76 to return to the neutral position of FIG. 3.

When cartridge 66 is inserted into cavity 60, cartridge surfaces 74 and 76 deflect toward each other due to their contact with a pair of tabs 98 positioned on thermal control unit 22 (FIG. 2). As noted, this deflection is resisted by the construction of cartridge 66, but not resisted so strongly as to require a user to exert undue inward force on cartridge 66 when inserting cartridge 66 into cavity 60. As cartridge 66 is inserted into cavity 60, angle 90 decreases from its neutral value shown in FIG. 3. This decrease of angle 90 continues as surfaces 74 and 76 are inserted past tabs 98.

Once past tabs 98, surfaces 74 and 76 are no longer constrained by the tabs from pivoting back to their neutral position. However, prior to surfaces 74 and 76 fully returning to their neutral position, surfaces 74 and 76 come into contact with cavity walls 62 and 64. Cavity walls 62 and 64 are angled with respect to each other at an angle 70 that is less than the neutral value of angle 90 of FIG. 3. As a result, cartridge 66 remains somewhat compressed by the smaller angle 70 of cavity walls 62 and 64. In this compressed state the inherent biasing of surfaces 74 and 76 back toward their neutral state urges surfaces 74 and 76 into tight contact with cavity walls 62 and 64. This tight contact substantially removes any air gaps between cartridge surfaces 74 and 76 and adjacent cavity walls 62 and 64, respectively, when cartridge 66 is received within cavity 60. The removal of such air gaps facilitates the exchange of thermal energy between heat exchanger 48 and the fluid within cartridge chamber 72.

Figure 4:
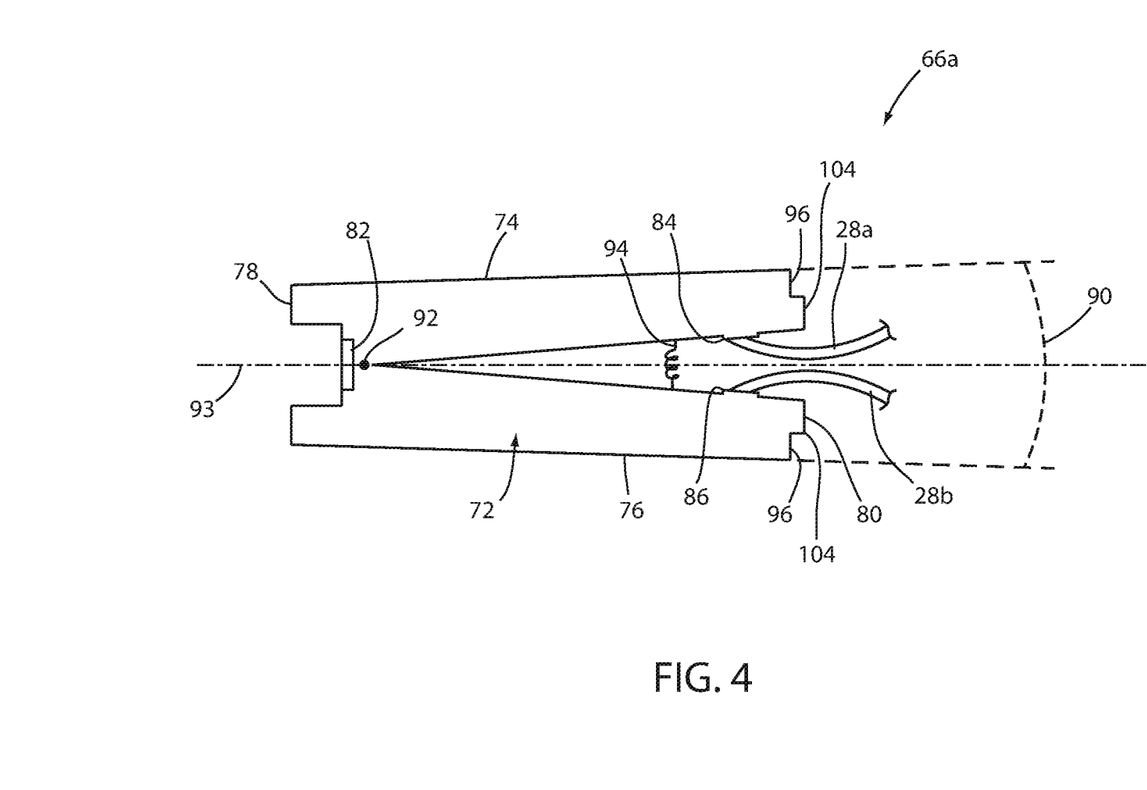
FIG. 4 is a cross-sectional schematic view of a fluid cartridge according to a second embodiment of the disclosure.

In an alternative embodiment shown in FIG. 4, a cartridge 66a includes a separate biasing element 94 adapted to bias cartridge surfaces 74 and 76 toward a neutral angle, such as an angle having the value of angle 90 in FIG. 3. In the embodiment illustrated in FIG. 4, the biasing element is in the form of a spring 94. Spring 94 exerts a biasing force that presses cartridge surfaces 74 and 76 against cavity walls 62 and 64, substantially removing any air gaps between cavity walls 62 and 64 and the cartridge surfaces 74 and 76. As noted, by substantially removing such air gaps, the exchange of thermal energy between heat exchanger 48 and the fluid within cartridge chamber 72 can be accomplished more quickly and efficiently.

Spring 94 may be positioned at locations other than where shown in FIG. 4, and one or more additional springs 94 may also be added. Spring(s) 94 supply all of the biasing force that urges cartridge 66a to return to its neutral orientation of FIG. 3. That is, cartridge 66a, unlike cartridge 66, does not include any internal construction that flexibly returns the cartridge to its neutral position, other than spring 94. In a modified embodiment of cartridge 66a, both springs 94 and the internal construction of cartridge 66a provide biasing forces that urge cartridge 66a back to its neutral position.

In order to further facilitate heat flow between heat exchanger 48 of thermal control unit 22 and cartridge 66 or 66a, cartridge surfaces 74 and 76 are constructed of a relatively thin material having good thermal conductance. In some embodiments, surfaces 74 and 76 are made from thin sheets of metal, such as copper, or the like. Due to their thin and flexible nature, cartridge surfaces 74 and 76 expand or bulge outwardly when pump head 82 rotates pump driver 83 in order to pump fluid through chamber 72. This pumping increases the fluid pressure inside of chamber 72 and causes cartridge surfaces 74 and 76 to bulge outwardly toward the adjacent cavity walls 62 and 64, further tightening the physical contact therebetween and facilitating the transfer of thermal energy between the fluid in chamber 72 and heat exchanger 48.

Cartridge front end 80 includes a pair of slots 96 that engage mating tabs 98 incorporated into cavity opening 68 to maintain cartridge 66 within cavity 60. Slots 96 and tabs 98 are configured such that when cartridge 66 or 66a is fully inserted within cavity 60 and cartridge surfaces 74 and 76 are at an angle that matches angle 70 of cavity 60, tabs 98 are received within slots 96 and prevent the cartridge from exiting from cavity 60. In another embodiment, the tabs are provided on cartridge front end 80 and the mating slots are provided at cavity opening 68 to maintain cartridge 66 or 66a within cavity 60.

Figure 5:
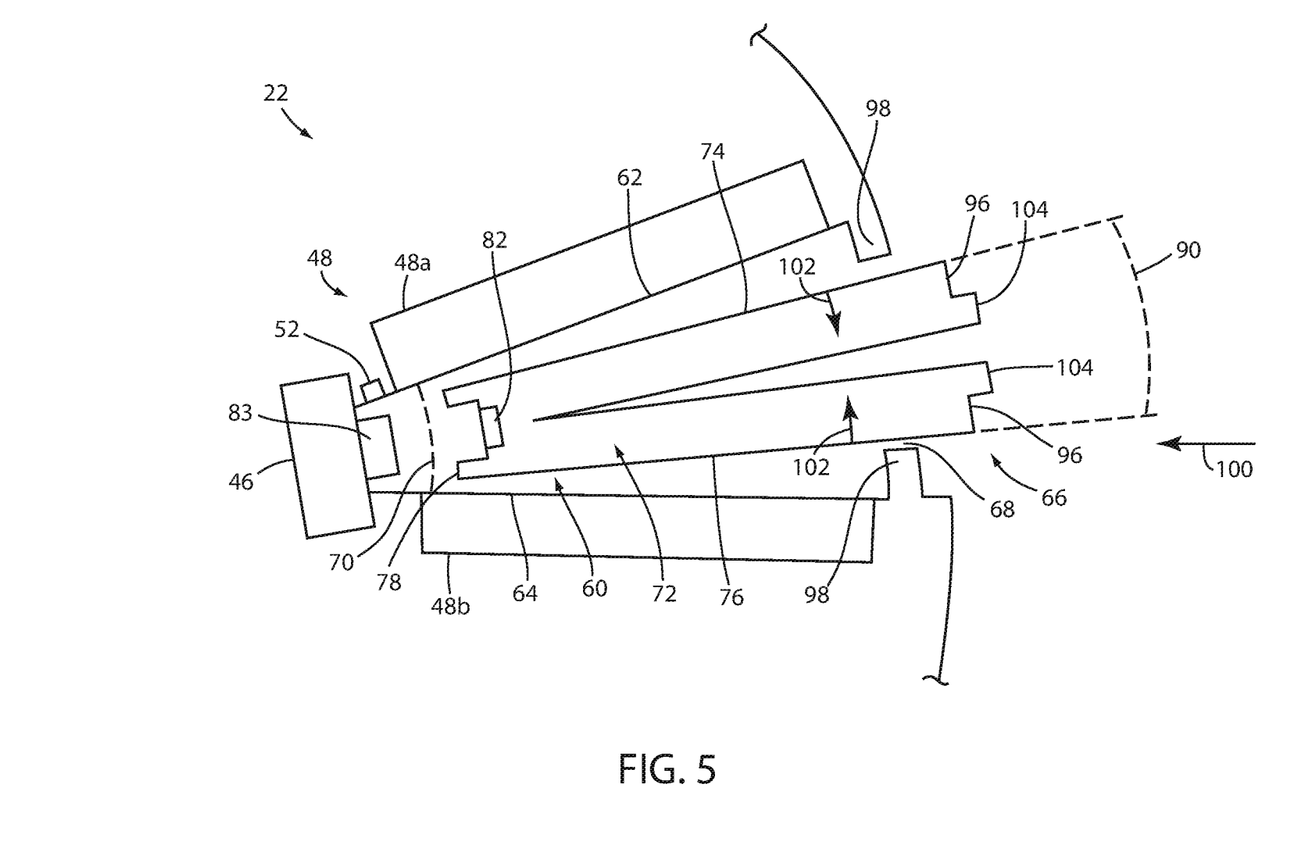
FIG. 5 is a cross-sectional view of the fluid cartridge of FIG. 2 shown being inserted into a portion of the thermal control unit of FIG. 2.
Figure 6:
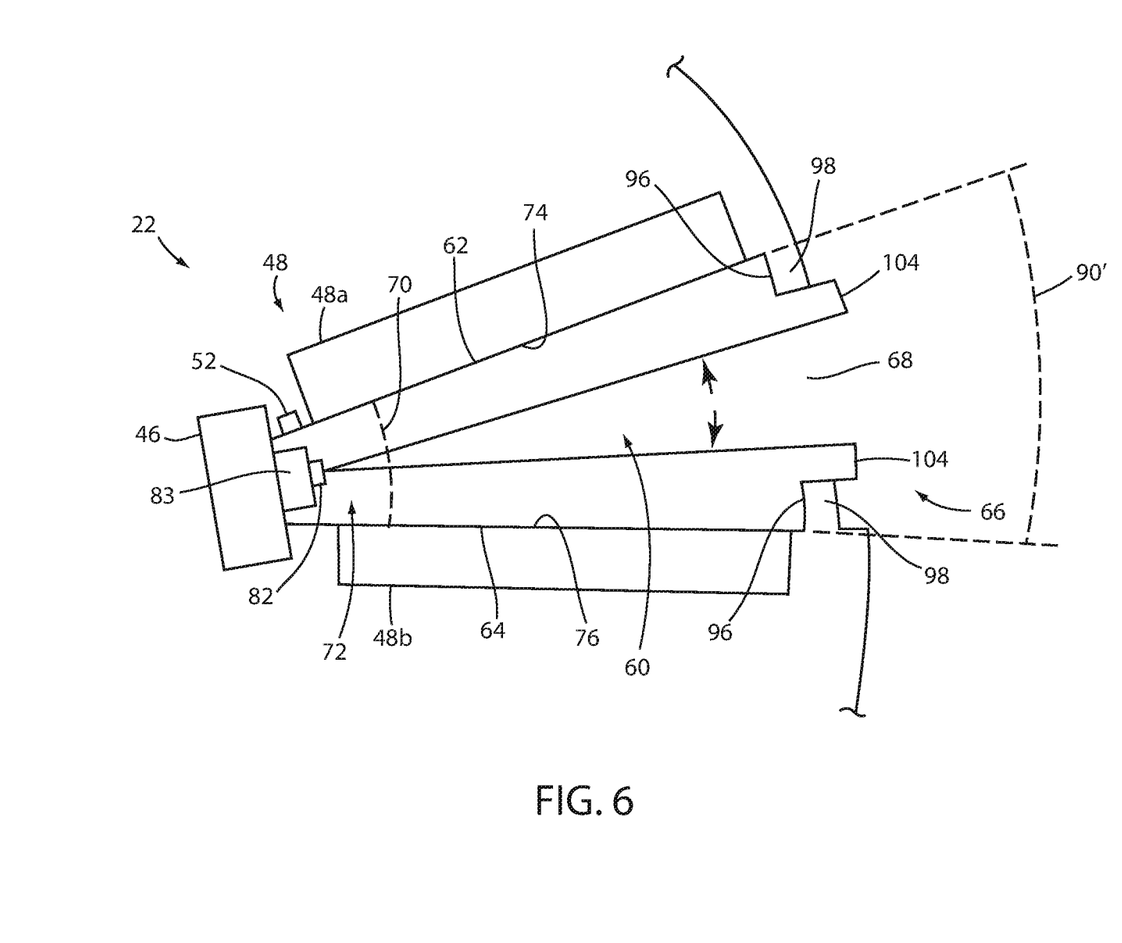
FIG. 6 is a cross-sectional view of the fluid cartridge of FIG. 2 shown after having been inserted into the thermal control unit of FIG. 2.

With reference now to FIGS. 5 and 6, a process for installing cartridge 66 in cavity 60 is described. This process is the same as for cartridge 66a, and therefore won't be repeated separately for cartridge 66a. Only relevant portions of thermal control unit 22 and cartridge 66 are illustrated in FIGS. 5 and 6 for ease of reference. To install cartridge 66, cartridge rear end 78 is inserted through cavity opening 68 in the direction illustrated by arrow 100 until pump head 82 engages pump driver 83 at an interior end of cavity 60. As cartridge 66 is inserted into cavity 60, cartridge surfaces 74 and 76 deflect toward one another, as illustrated by arrows 102, to decrease angle 90 sufficiently to pass by tabs 98. After passing by tabs 98, surfaces 74 and 76 expand outwardly to abut against walls 62 and 64 at an angle that substantially matches angle 70. In one embodiment, both sides of cartridge 66 are provided with projections 104 that are adapted to be gripped by a user to compress cartridge surfaces 74 and 76 together for insertion and removal of cartridge 66. Projections 104 can be used by a user to press cartridge surfaces 74 and 76 together against the cartridge bias to provide clearance for inserting cartridge 66 through cavity opening 68.

Referring now to FIG. 6, once cartridge 66 (or 66a) is fully inserted into cavity 60 and any user applied compressive force on cartridge surfaces 74 and 76 is removed, the cartridge bias applies a force urging cartridge surfaces 74 and 76 to return to their neutral position (e.g. angle 90 of FIG. 3). Engagement between cartridge surfaces 74 and 76 and adjacent cavity walls 62 and 64 prevents cartridge surfaces 74 and 76 from returning completely to their neutral angle and limits cartridge surfaces 74 and 76 to an angle 90' that generally matches cavity wall angle 70. In those embodiments in which cartridge surfaces 74 and 76 include portions that expand under pressure as fluid is pumped through cartridge 66, any air gaps between surfaces 74 and 76 and their adjacent walls 62 and 64 that remain after cartridge 66 is inserted in cavity 60 may be removed through the outward bulging of cartridge surfaces 74 and 76 caused by the fluid being pumped through the cartridge 66. This fluid pressure bulging, in addition to the cartridge biasing, ensures physical contact between cartridge surfaces 74 and 76 and adjacent cavity walls 62, which facilitates efficient thermal transfer between heat exchanger 48 and the fluid within cartridge 66.

When cartridge 66 is fully inserted within cavity 60, cartridge surfaces 74 and 76 expand away from one another, resulting in tabs 98 being received within cartridge slots 96 and thereby retaining cartridge 66 within cavity 60. The engagement between slots 96 and tabs 98 prevents cartridge 66 from exiting from cavity 60 until cartridge 66 is removed by the user. In this manner, insertion and securing of cartridge 66 occurs in a single motion with no additional steps or movements required for a user to secure cartridge 66 within cavity 60. In this manner, cartridge 66 can be installed within cavity 60 and ready for use with minimal effort required of the user. To remove cartridge 66 from within cavity 60, the user grasps projections 104 and compresses cartridge surfaces 74 and 76 toward one another, against the cartridge bias, to disengage cartridge slots 96 from tabs 98. The user then withdraws cartridge 66 through opening 68 to remove cartridge 66 from cavity 60.

Both cartridge 66 and 66a are vertically symmetrical in the illustrated embodiments. That is, cartridges 66 and 66a are symmetrical about a plane extending through midline 93 (FIG. 4) that is perpendicular to the plane of the page of FIG. 4. Thus, cartridge 66 (and 66a) can be inserted into cavity 60 in the manner illustrated in FIGS. 5 and 6, or they can be flipped upside down and still inserted in the manner illustrated. When flipped upside down, cartridges 66 and 66a are received within cavity 60 with cartridge surface 74 adjacent cavity wall 64, and cartridge surface 76 adjacent cavity wall 62. The user can therefore insert and retain cartridges 66 and 66a within cavity 60 in a single step, without paying attention to the directionality of the cartridge.

In other embodiments, either or both of cartridges 66 and 66a are vertically and/or horizontally asymmetrical, requiring the cartridge to be inserted in a particular orientation. In some of these modified embodiments, the cartridge and/or thermal control unit may be defined such that insertion of the cartridge in a different orientation leads to different functions. In one such example, if heating of the fluid is desired, the cartridge is inserted in a first orientation, and if cooling is desired, the cartridge is inserted in a second and different orientation.

While cavity 60 has been described as having walls 62 and 64 which are at a fixed angle 70, in some embodiments, cavity walls 62 and 64 include a moveable portion which is biased toward angle 70. In other words, instead of having cartridge surfaces 74 and 76 flex so as to move into physical contact with cavity walls 62 and 64, cavity walls 62 may be flexible so as to move into contact with cartridge surfaces 74 and 76. As yet another alternative, both cavity walls 62 and 62 and cartridge surfaces 74 and 76 may be flexible and biased toward each other in order to ensure tight physical contact with each other. When cavity walls 62 and 64 are flexible, they may be configured with a moveable hinge and/or a spring to bias themselves toward angle 70. As the cartridge is inserted into cavity 60, cavity walls 62 and 64 deflect to receive the cartridge therein. The bias on cavity walls 62 and 64 exerts a force that presses walls 62 and 64 toward adjacent cartridge surfaces 74 and 76 to remove any gap therebetween, thereby facilitating thermal transfer between cavity walls 62 and 64 and adjacent surfaces 74 and 76.

Figure 7:
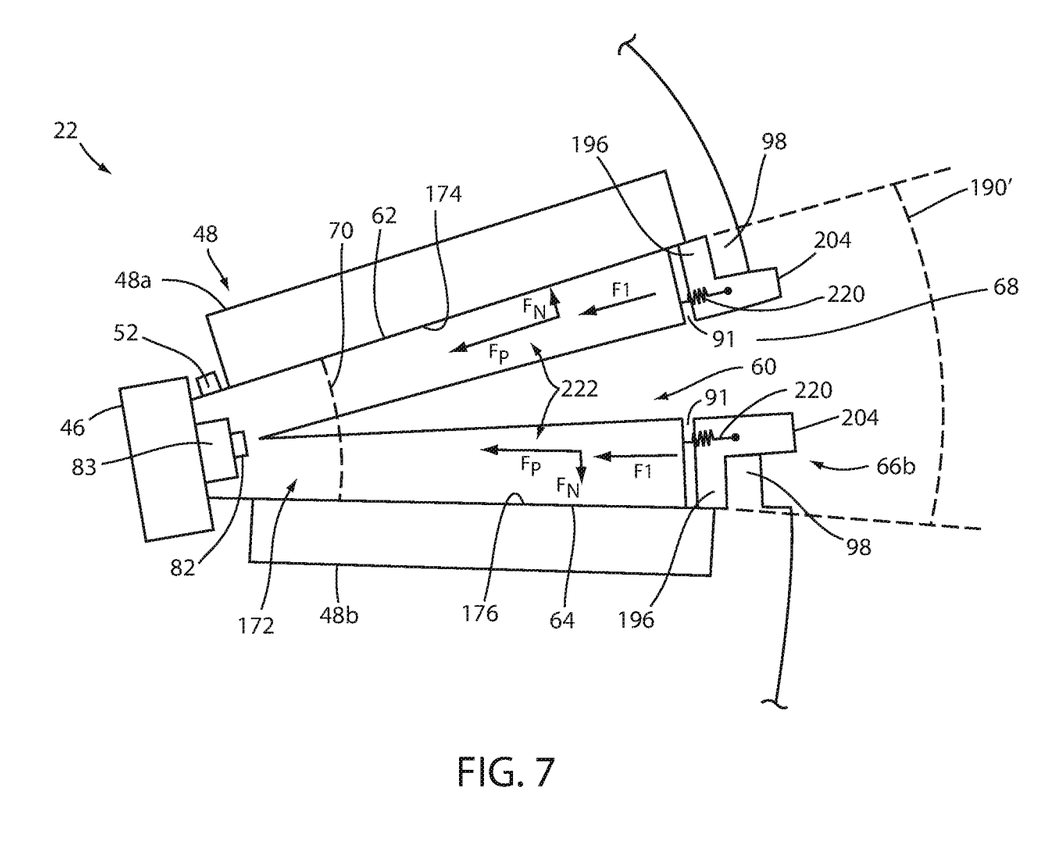
FIG. 7 is a cross-sectional schematic view of a fluid cartridge according to a third embodiment shown after having been inserted into the thermal control unit of FIG. 2.

Referring now to FIG. 7, a third embodiment of a fluid cartridge 66b is illustrated. Those components of fluid cartridge 66b that are the same as fluid cartridges 66 or 66a are identified with the same reference number increased by 100 and, unless otherwise stated, operate in the same manner. Those components that are new to fluid cartridge 66b are provided with a new reference number. Any of the functions and/or components of fluid cartridges 66 or 66a that are not present in fluid cartridge 66b can be incorporated into fluid cartridge 66b and vice versa.

Fluid cartridge 66b includes a pair of movable ends 196 that are received behind cavity tabs 98 when cartridge 66b is fully inserted into cavity 60. Each movable end 196 is coupled to a main body portion 222 of cartridge 66b by way of a biasing element 220, such as, but not limited to, a spring 220. Springs 220 are configured such that in their neutral state (i.e. not compressed or extended), each movable end 196 is spaced away from body portion 222 by a gap 91. The size of gap 91 changes depending upon the forces exerted on cartridge 66b. In the position illustrated in FIG. 7, gap 91 is compressed from its neutral state. Thus, in the position shown in FIG. 7, springs 220 exert a force F1 against the main body portion 222 of cartridge 66b that, as discussed more below, urges surfaces 174 and 176 into contact with walls 62 and 64.

Once the cartridge 66b is fully inserted into cavity 60 and a user has released moving ends 196, springs 220 urge moving ends 196 away from body portion 222. This movement pushes movable ends 196 into engagement with a rear surface of tabs 98. This engagement prevents cartridge 66b from exiting from cavity 60. Further, the engagement of movable ends 196 with the rear surface of tabs 98 occurs prior to each spring 220 fully returning to its neutral state. As a result, a force F1 is exerted by each spring upon body portion 222 in the direction indicated. Forces F1 are oriented at oblique angles with respect to the planes defined by cavity walls 62 and 64. Forces F1 can therefore be resolved into a normal component (Fn) that is perpendicular to the plane of the adjacent wall (62 or 64) and a parallel component (Fp) that is parallel to the plane of the adjacent wall (62 or 64). The normal component Fn urges surfaces 174 and 176 into snug contact with cavity walls 62 and 64. Thus, it can be seen that movable ends 196 are constructed such that when springs 220 are under compression, the force F1 exerted by the expansion of springs 220 in a first generally inward direction into cavity 60 is partially redirected in a second directions (the directions of forces Fn) that urge surfaces 174 and 176 into contact with the interior of cavity 60.

To remove cartridge 66b from within cavity 60, the user grasps projections 204, pushes ends 196 against the bias of springs 220, and compresses cartridge surfaces 174 and 176 toward one another to disengage cartridge ends 196 from tabs 98. The user compresses cartridge surfaces 174 and 176 sufficiently to provide clearance between cartridge 66b and cavity opening 68. The user then withdraws cartridge 66b through opening 68 to remove cartridge 66b from cavity 60.

In another embodiment, the location of ends 196 and tabs 98 are reversed. In this embodiment, cartridge 66b includes a slot that is adapted to receive a movable tab incorporated into cavity 60 that retains cartridge 66b within cavity 60. Spring 220 is incorporated into the movable tab in the cavity and exerts a force on cartridge 66b directed toward the interior of cavity 60.

In still another alternative embodiment, a thermal control system for controlling a temperature of a fluid delivered to a patient is provided where the biasing of the cartridge surfaces into contact with the cavity walls is carried out exclusively through the bulging or expansion of the cartridges surfaces. In this alternative embodiment, the thermal control unit includes at least the following: a housing comprising a cavity having opposing walls, a heat exchanger positioned within the housing adjacent the cavity, a cartridge adapted to be removably received within the cavity; and cartridge surfaces that are adapted to flex outwardly toward the cavity walls due to the internal fluid pressure of the fluid inside the cartridge. Thus, when the pump within the cartridge is energized, the resulting increase in the fluid pressure urges the cartridge walls into contact with the cavity walls. No separate and/or additional biasing element is needed in this alternative embodiment.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control system for controlling a temperature of a fluid delivered to a patient, the thermal control system comprising:
    a housing comprising a cavity having opposing walls;
    a heat exchanger positioned within the housing adjacent the cavity;
    a cartridge having opposing surfaces defining a chamber therebetween for housing the fluid, the cartridge adapted to be removably received within the cavity; and
    a biasing element incorporated into the cartridge and adapted to bias the opposing surfaces away from one another and into contact with the opposing walls, wherein when the cartridge is received within the cavity, thermal energy is transferred between the heat exchanger and the fluid housed within the cartridge.

2. The thermal control system of claim 1 wherein the biasing element comprises a spring.

3. The thermal control system of claim 1 wherein the biasing element comprises a living hinge formed in the cartridge.

4. The thermal control system of claim 1 wherein:
    one of the cavity and the cartridge includes a tab and the other of the cavity and the cartridge includes a mating slot, and
    wherein the tab engages the slot when the cartridge is inserted into the cavity and retains the cartridge within the cavity.

5. The thermal control system of claim 4 wherein the tab is biased toward the slot.

6. The thermal control system of claim 5 wherein:
    the cartridge includes projections that extend beyond an opening to the cavity when the cartridge is received within the cavity, and
    wherein the projections are adapted to be grasped to press the opposing surfaces toward one another, against the bias, to disengage the tab from the slot.

7. The thermal control system of claim 1 wherein the opposing surfaces include a flexible portion adapted to expand outward under pressure.

8. A thermal control system for controlling a temperature of a fluid delivered to a patient, the thermal control system comprising:
    a housing comprising a cavity having opposing walls and an opening therebetween, the opposing walls oriented at a first angle relative to one another such that a distance between the opposing walls decreases with increasing depth in the cavity;
    a heat exchanger positioned within the housing adjacent the cavity; and
    a cartridge having a pair of opposing surfaces defining a chamber therebetween for housing the fluid, the cartridge adapted to be removably received within the cavity through the opening, wherein the opposing surfaces are oriented at a second angle relative to one another, the second angle greater than the first angle, and wherein when the cartridge is received within the cavity, one or both of the first and second angles change such that no air gaps exist between the opposing surfaces and the opposing walls, and wherein thermal energy is transferred between the heat exchanger and the fluid housed within the cartridge.

9. The thermal control system of claim 8 wherein the opposing surfaces are adapted to deflect as the cartridge is inserted into the cavity through the opening.

10. The thermal control system of claim 8 wherein the cartridge includes a biasing element biasing the opposing surfaces into the second angle, and wherein the opposing surfaces are moveable toward one another, against the bias, to a third angle at least as small as the first angle.

11. The thermal control system of claim 10 wherein the biasing element comprises one of a spring and a living hinge formed in the cartridge.

12. The thermal control system of claim 8 wherein one of the cavity and the cartridge includes a tab and the other of the cavity and the cartridge includes a mating slot, and wherein the tab engages the slot when the cartridge is inserted into the cavity and retains the cartridge within the cavity.

13. The thermal control system of claim 12 wherein the tab is biased toward the slot.

14. The thermal control system of claim 13 wherein:
the cartridge includes a pair of projections that extends beyond the opening to the cavity when the cartridge is received within the cavity, and
wherein the projections are adapted to be grasped to press the opposing surfaces toward one another, against the bias, to disengage the tab from the slot.

15. The thermal control system of claim 8 wherein the opposing surfaces include a flexible portion adapted to expand outward under pressure.

16. A thermal control system for controlling a temperature of a fluid delivered to a patient, the thermal control system comprising:
a housing comprising a cavity having opposing walls and an opening therebetween;
a heat exchanger positioned within the housing adjacent the cavity;
a cartridge having opposing surfaces defining a chamber therebetween for housing the fluid, the cartridge adapted to be removably received within the cavity through the opening; and
a biasing element incorporated into one of the housing or the cartridge and adapted to exert a first force urging the cartridge in a first direction into the opening, wherein the cartridge is adapted to direct a component of the first force in a second direction different from the first direction, the component of the first force urging the opposing surfaces into contact with the opposing walls such that when the cartridge is received within the cavity, thermal energy is transferred between the heat exchanger and the fluid housed within the cartridge.

17. The thermal control system of claim 16 wherein the biasing element comprises a spring.

18. The thermal control system of claim 16 wherein the opposing surfaces are biased away from one another.

19. The thermal control system of claim 18 wherein the cartridge comprises a spring or a living hinge adapted to bias the opposing surfaces.

20. The thermal control system of claim 16 wherein:
the opposing walls are oriented at a first angle relative to one another; and
the opposing surfaces are oriented at a second angle relative to one another, the second angle greater than the first angle, and
wherein when the cartridge is received within the cavity, one or both of the first and second angles change such that no air gaps exist between the opposing surfaces and the opposing walls.

21. The thermal control system of claim 16 wherein the opposing surfaces include a flexible portion adapted to expand outward under pressure.

* * * * *